(12) United States Patent
Groat

(10) Patent No.: US 7,291,338 B2
(45) Date of Patent: Nov. 6, 2007

(54) METHOD AND DEVICE FOR DETECTING FELINE IMMUNODEFICIENCY VIRUS

(75) Inventor: Randall Groat, Freeport, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 233 days.

(21) Appl. No.: 11/075,480

(22) Filed: Mar. 9, 2005

(65) Prior Publication Data

US 2006/0205923 A1    Sep. 14, 2006

(51) Int. Cl.
  *A61K 39/21*   (2006.01)
  *A61K 39/00*   (2006.01)
  *A61K 39/88*   (2006.01)
  *G01N 33/00*   (2006.01)
  *G01N 33/53*   (2006.01)

(52) U.S. Cl. .............. 424/188.1; 424/184.1; 424/185.1; 424/186.1; 424/187.1; 435/4; 435/5; 435/7.1; 435/7.9; 435/7.92

(58) Field of Classification Search ............ None
See application file for complete search history.

(56) References Cited

U.S. PATENT DOCUMENTS

| | | | |
|---|---|---|---|
| 4,629,783 A | 12/1986 | Cosand | |
| 4,879,212 A | 11/1989 | Wang et al. | |
| 4,900,548 A | 2/1990 | Kitchen | |
| 5,037,753 A | 8/1991 | Pedersen et al. | |
| 5,118,602 A | 6/1992 | Pedersen et al. | |
| 5,177,014 A | 1/1993 | O'Connor et al. | |
| 5,219,725 A | 6/1993 | O'Connor et al. | |
| 5,565,319 A | 10/1996 | Pedersen et al. | |
| 5,576,177 A | 11/1996 | Fridland et al. | |
| 5,591,572 A | 1/1997 | Kemp et al. | |
| 5,627,026 A | 5/1997 | O'Connor et al. | |
| 5,648,209 A | 7/1997 | Avrameas et al. | |
| 5,656,732 A | 8/1997 | Andersen et al. | |
| 5,705,331 A | 1/1998 | Arthur et al. | |
| 5,726,013 A | 3/1998 | Clark | |
| 5,736,378 A | 4/1998 | Elder et al. | |
| 5,750,333 A | 5/1998 | Clark | |
| 5,820,869 A | 10/1998 | Wasmoen et al. | |
| 5,833,993 A | 11/1998 | Wardley | |
| 5,846,825 A | 12/1998 | Yamamoto | |
| 5,849,303 A | 12/1998 | Wasmoen et al. | |
| 5,994,516 A | 11/1999 | Pancino et al. | |
| 6,077,662 A | 6/2000 | Compans et al. | |
| 6,228,608 B1 | 5/2001 | Young et al. | |
| 6,254,872 B1 | 7/2001 | Yamamoto | |
| 6,284,253 B1 | 9/2001 | Barr et al. | |
| 6,300,118 B1 | 10/2001 | Chavez et al. | |
| 6,331,616 B1 | 12/2001 | Tompkins et al. | |
| 6,383,765 B1 | 5/2002 | Andersen et al. | |
| 6,391,304 B1 | 5/2002 | Richardson et al. | |
| 6,447,993 B1 | 9/2002 | Yamamoto | |
| 6,455,265 B1 | 9/2002 | Serres | |
| 6,458,528 B1 | 10/2002 | Groat et al. | |
| 6,503,713 B1 | 1/2003 | Rana | |
| 6,613,530 B1 | 9/2003 | Wienhues et al. | |

FOREIGN PATENT DOCUMENTS

| | | |
|---|---|---|
| EP | 0 602 406 B1 | 11/1997 |
| EP | 0 962 774 A1 | 12/1999 |
| WO | WO90/06510 | 6/1990 |
| WO | WO/90/13573 | 11/1990 |
| WO | WO92/09632 | 6/1992 |
| WO | WO92/22573 | 12/1992 |
| WO | WO93/01304 | 1/1993 |
| WO | WO94/02612 | 2/1994 |
| WO | WO94/06471 | 3/1994 |
| WO | WO96/40268 | 12/1996 |
| WO | WO96/40953 | 12/1996 |
| WO | WO96/40956 | 12/1996 |
| WO | WO96/40957 | 12/1996 |
| WO | WO97/07817 | 3/1997 |
| WO | WO99/29182 | 6/1999 |
| WO | WO 01/04280 | 1/2001 |
| WO | WO 03/015814 | 2/2003 |
| WO | WO 2004/100985 | 11/2004 |

OTHER PUBLICATIONS

Wimley, William, et al., *Designing Transmembrane α-Helices that insert Spontaneously*, Biochemistry, 39:4432-4442 (2000).

Ponsati, Berta, et al., *A Synthetic Strategy for Simulatenous Purification-Conjugation of Antigenic Peptides*, Analytical Biochemistry, 181:389-395 (1989).

Rimmelzwaan, G.F., et al., *gag-And env-specific serum antibodies in cats after natural and experimental infection with feline immunodeficincy virus*, Veterinary Microbiology, 39:153-165 (1994).

Calzolari, Marialaura, et al., *Serological diagnosis of feline immunodeficiency virus infection using recombinant transmembrane glycoprotein*, Veterinary Immunology and Immunopathology, 46:83-92 (1995).

U.S. Appl. No. 10/938,097, filed Sep. 10, 2004, Groat et al.
U.S. Appl. No. 10/938,056, filed Sep. 10, 2004, Groat et al.
U.S. Appl. No. 11/015,675, filed Dec. 17, 2004, Groat et al.
U.S. Appl. No. 11/059,285, filed Feb. 16, 2005, Groat et al.

(Continued)

*Primary Examiner*—Jeffrey S. Parkin
*Assistant Examiner*—Louise Humphrey
(74) *Attorney, Agent, or Firm*—McDonnell Boehnen Hulbert & Berghoff LLP

(57) ABSTRACT

FIV gag polypeptides and a method and device for determining a feline immunodeficiency virus infection in an animal. The method includes contacting a biological sample from a felid with the FIV polypeptides and determining the binding of antibodies in the sample to the polypeptides. A device for detecting FIV antibodies is provided.

15 Claims, No Drawings

OTHER PUBLICATIONS

U.S. Appl. No. 11/076,820, filed Mar. 10, 2005, Groat et al.
U.S. Appl. No. 11/077,321, filed Mar. 10, 2005, Groat et al.
U.S. Appl. No. 11/075,958, filed Mar. 9, 2005, Groat et al.
Olmsted, R.A. et al, "Molecular cloning of the feline immunodeficiency virus", *Proc. Natl. Acad. Sci. USA*, 1989, vol. 86, pp. 2448-2452.
Maki, N. et al., "Molecular Characterization and Heterogeneity of Feline Immunodeficiency Virus Isolates", *Archives of Virolology*, 1992, vol. 123, pp. 29-45.
Yamamoto, J.K. et al., "Experimental Vaccine Protection against Homologous and Heterologous Strains of Feline Immunodeficiency Virus", *Journal of Virology*, 1993, vol. 67, No. 1, pp. 601-605.
Hohdatsu, T. et al., "Effect of Dual-subtype Vaccine Against Feline Immunodeficiency Virus Infection", *Veterinary Microbiology*, 1997, vol. 58, pp. 155-165.
Uhl, E.W. et al., "FIV Vaccine Development and its Importance to Veterinary and Human Medicine: A Review FIV Vaccine 2002 Update and Review", *Veterinary Immunology and Immunopathology*, 2002, vol. 90, pp. 133-132.
Murray, D.M., "Identifying FIV Vaccinates", *Journal of the American Veterinary Medical Association*, 2003, vol. 222, p. 710.
Moon, D., "Another Solution to Identify FIV-Vaccinated Cats", *Journal of the American Veterinary Medical Association*, 2003, vol. 22, No. 9, p. 1207.
Calandrella, M., "Desitometric Analysis of Western Blot Assays for Feline Immunodeficiency Virus Antibodies", *Veterinary Immunology and Immunopathology*, 2001, vol. 79, pp. 261-271.
Hartmann, K. et al., "Comparison of Six In-House Tests for the Rapid Diagnosis of Feline Immunodeficiency and Feline Leukemia Virus Infections", *The Veterinary Record*, 2001, vol. 149, pp. 317-320.
Richardson, J., et al., "Delayed Infection after Immunization with a peptide from the Transmembrane Glycoprotein of the Feline Immunodeficiency Virus", *Journal of Virology*, 1998, vol. 72, pp. 2406-2415.
Finerty, Susan, et al., "Mucosal immunization with experimental feline immunodeficiency virus (FIV) vaccines induces both antibody and T cell responses but does not protect against rectal FIV challenge", *Vaccine*, 2000, vol. 18, pp. 3254-3265.
DeRonde, Anthony, et al., "Antibody Response in Cats to the Envelope Proteins of Feline Immunodeficincy Virus: identification of an Immunodominant Neutralization Domain", *Virology*, 1994, vol. 198, pp. 257-264.
Lombardi, Stefania, et al., "Identification of a Linear Neutralization Site within the Third Variable region of the Feline Immunodeficiency Virus Envelope", *Journal of Virology*, 1993, vol. 67, pp. 4742-4749.
Avrameas, A., et al., "Localisation of Three Epitopes of the ENV Protein of Feline Immunodeficiency Virus", *Molecular Immunology*, 1992, vol. 29, pp. 565-572.
Avrameas, A., et al., "Serological Diagnosis of Feline Immunodeficiency Virus Infection Based on Synthetic Peptides from Env Glycoproteins", *Res. Virol*, 1993, vol. 144, pp. 209-218.
Olmsted, Robert, "Nucleotide Sequence Analysis of Feline Immunodeficiency Virus: Genome Organization and Relationship to Other Lentiviruses", *Proc. Natl. Acad. Sci. USA*, 1989, vol. 86, pp. 8088-8092.
Gallaher, William, et al., "A General Model for the Transmembrane Proteins of HIV and Other Retroviruses", *AIDS Research and Human Retroviruses*, 1989, vol. 5, pp. 431-440.
Mermer, B., et al., "Similarities Between the Transmembrane Proteins of FIV and HIV", *Abstract distributed on and Poster Presentation during the Cold Spring Harbor Conference*, 1991.
Javaherian, et al., "Principal neutralizing domain of the human immunodeficiency virus type 1 envelope protein", *Proc. Natl. Acad. Sci. USA*, 1989, vol. 86, pp. 6768-6772.
Steinman, et al., "Biochemical and Immunological Characterization of the Major Structural Proteins of Feline Immunodeficiency Virus", *Journal of General Virology*, 1990, vol. 71, pp. 701-706.
Gnann, et al, "Fine Mapping of an Immunodominant Domain in the Transmembrane Glycoprotein of Human Immunodeficiency Virus", *Journal of Virology*, 1987, vol. 61, pp. 2639-2641.
Chong, et al., "Analysis of Equine Humoral Immune Responses to the Transmembrane Envelope Glycoprotein (gp45) of Equine Infectious Anemia Virus", *Journal of Virology*, 1991, pp. 1013-1018.
Berton, et al., "The Antigenic Structure of the Influenza B Virus Hemagglutinin: Operational and Topological Mapping with Monoclonal Antibodies", *Virology*, 1985, vol. 143, pp. 583-594.
Mermer, et al., "A Recombinant-based Feline Immunodeficiency Virus Antibody Enzyme-Linked Immunosorbent Assay", *Veterinary Immunology and Immunopathology*, 1992, vol. 35, pp. 133-141.
Massi, et al., "Most Potential Linear B Cell Epitopes of Env Glycoproteins of Feline Immunodeficiency Virus are Immunogenically Silent in Infected Cats", *AIDS Research and Human Retroviruses*, 1997, vol. 13, pp. 1121-1129.
Lutz, et al., "FIV Vaccine Studies I, Immune Response to Recombinant FIV ENV Gene Products and Outcome After Challenged Infection", *Veterinary Immunology and Immunopathology*, 1995, vol. 46, pp. 103-113.
Tijhaar, Edwin, et al., "Salmonella Typhimurium AroA Recombinants and Immune-stimulating Complexes as Vaccine Candidates for Feline Immunodeficiency Virus", *Journal of General Virology*, 1997, vol. 78(12), pp. 3265-3275.
Fort Dodge Animal Health, First Feline Aids Vaccine Available, Press Release, Aug. 12, 2002.
Fel-O-Vax® FIV Product Brochure, 2002 Fort Dodge Animal Health.

```
                         SEQUENCE LISTING

<160> NUMBER OF SEQ ID NOS: 9

<210> SEQ ID NO 1
<211> LENGTH: 36
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p24.

<400> SEQUENCE: 1

Lys Met Val Ser Ile Phe Met Glu Lys Ala Arg Glu Gly Leu Gly Gly
1               5                   10                  15

Glu Glu Val Gln Leu Trp Phe Thr Ala Phe Ser Ala Asn Leu Thr Pro
            20                  25                  30

Thr Asp Met Ala
        35

<210> SEQ ID NO 2
<211> LENGTH: 36
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p24.

<400> SEQUENCE: 2

Glu Ile Leu Asp Glu Ser Leu Lys Gln Met Thr Ala Glu Tyr Asp Arg
1               5                   10                  15

Thr His Pro Pro Asp Gly Pro Arg Pro Leu Pro Tyr Phe Thr Ala Ala
            20                  25                  30

Glu Ile Met Gly
        35

<210> SEQ ID NO 3
<211> LENGTH: 39
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p24.

<400> SEQUENCE: 3

Lys Ala Lys Ser Pro Arg Ala Val Gln Leu Arg Gln Gly Ala Lys Glu
1               5                   10                  15

Asp Tyr Ser Ser Phe Ile Asp Arg Leu Phe Ala Gln Ile Asp Gln Glu
            20                  25                  30

Gln Asn Thr Ala Glu Val Lys
        35

<210> SEQ ID NO 4
<211> LENGTH: 41
<212> TYPE: PRT
<213> ORGANISM: Feline immunodeficiency virus
<220> FEATURE:
<221> NAME/KEY: MISC_FEATURE
```

```
<223> OTHER INFORMATION: Polypeptide derived from the native FIV gag
      p24.

<400> SEQUENCE: 4

Glu Tyr Asp Arg Thr His Pro Pro Asp Gly Pro Arg Pro Leu Pro Tyr
1               5                   10                  15

Phe Thr Ala Ala Glu Ile Met Gly Ile Gly Leu Thr Gln Glu Gln Gln
            20                  25                  30

Ala Glu Ala Arg Phe Ala Pro Ala Arg
        35                  40

<210> SEQ ID NO 5
<211> LENGTH: 36
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p15.

<400> SEQUENCE: 5

Met Gly Asn Gly Gln Gly Arg Asp Trp Lys Met Ala Ile Lys Arg Cys
1               5                   10                  15

Ser Asn Val Ala Val Gly Val Gly Lys Ser Lys Lys Phe Gly Glu
            20                  25                  30

Gly Asn Phe Arg
        35

<210> SEQ ID NO 6
<211> LENGTH: 39
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p15.

<400> SEQUENCE: 6

Glu Gly Asn Phe Arg Trp Ala Ile Arg Met Ala Asn Val Ser Thr Gly
1               5                   10                  15

Arg Glu Pro Gly Asp Ile Pro Glu Thr Leu Asp Gln Leu Arg Leu Val
            20                  25                  30

Ile Cys Asp Leu Gln Glu Arg
        35

<210> SEQ ID NO 7
<211> LENGTH: 45
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p15.

<400> SEQUENCE: 7

Glu Thr Leu Asp Gln Leu Arg Leu Val Ile Cys Asp Leu Gln Glu Arg
1               5                   10                  15

Arg Glu Lys Phe Gly Ser Ser Lys Glu Ile Asp Met Ala Ile Val Thr
            20                  25                  30

Leu Lys Val Phe Ala Val Ala Gly Leu Leu Asn Met Thr
        35                  40                  45

<210> SEQ ID NO 8
```

-continued

```
<211> LENGTH: 35
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p15.

<400> SEQUENCE: 8

Leu Leu Asn Met Thr Val Ser Thr Ala Ala Ala Ala Glu Asn Met Tyr
1               5                   10                  15

Ser Gln Met Gly Leu Asp Thr Arg Pro Ser Met Lys Glu Ala Gly Gly
                20                  25                  30

Lys Glu Glu
        35

<210> SEQ ID NO 9
<211> LENGTH: 25
<212> TYPE: PRT
<213> ORGANISM: Feline immunodeficiency virus
<220> FEATURE:
<221> NAME/KEY: MISC_FEATURE
<223> OTHER INFORMATION: Polypeptide derived from the native FIV gag
      p15.

<400> SEQUENCE: 9

Lys Glu Glu Gly Pro Pro Gln Ala Tyr Pro Ile Gln Thr Val Asn Gly
1               5                   10                  15

Val Pro Gln Tyr Val Ala Leu Asp Pro
                20                  25
```

METHOD AND DEVICE FOR DETECTING FELINE IMMUNODEFICIENCY VIRUS

FIELD OF THE INVENTION

The invention is related to the detection of antibodies directed to Feline Immunodeficiency Virus.

BACKGROUND OF THE INVENTION

Feline immunodeficiency virus (FIV), formerly called feline T-lymphotrophic lentivirus, was first isolated in 1986 from a large multiple cat household in Petaluma, Calif. (Pederson et al., Science (1987) 235:790). FIV infects cats to produce an AIDS-like syndrome. Although FIV is morphologically and pathologically similar to the human immunodeficiency virus (HIV), it has been shown to be antigenically distinct from HIV. Like HIV, once a cat becomes infected with FIV, the disease progresses from a primary infection (viraemia, fever, general lymphadenitis) to a lengthy asymptomatic phase, followed by severe impairment in immune function caused by a reduction in CD4 lymphocytes, and resulting in heightened susceptibility to secondary infections and ultimately death.

FIV has been classified as a member of the subfamily Lentiviridae in the family Retroviridae, the family that includes human and simian immunodeficiency viruses, equine infectious anaemia, maedi visna of sheep and caprinearthritis encephalitis viruses (CAEV). The genome of FIV is organized like other lentiviruses with three long open reading frames corresponding to gag, pol and env (Talbott et al., Proc. Natl. Acad. Sci. (1989) 86:5743; Olmsted et al., Proc. Natl. Acad. Sci. (1989) 86:2448). The gag gene codes for the major structural components of the virus, the env gene codes for the envelope glycoprotein, and the pol gene codes for the polymerase protein.

The gag gene is expressed as a 55 kD polyprotein that is processed into three subunits: a p15 matrix protein, a p24 capsid protein, and a p10 nucleocapsid protein. The pol gene encodes three proteins: the protease, reverse transcriptase and a p14.6 protein of unknown function. Autoprocessing by the protease portion of the gene gives rise to all three proteins of the pol region. Additionally, the protease is responsible for the processing of the gag precursor. The pol gene is expressed as a gag-pol fusion protein. The envelope gene is expressed as a 160 kD glycoprotein, gp160. The antigenicity of the FIV core proteins is similar to other lentiviruses.

Several independent viral isolates have been prepared across the world, and a certain number of studies have been carried out in order to demonstrate the structure of the isolated strains: the American strain Petaluma, Talbott et al. Natl. Acad. Sci. USA, 1989, 86, 5743-5747; Philipps et al., J. Virol., 1990, 64, 10, 4605-4613), the Japanese strains (the TM1 and TM2 strains), Miyazawa et al., Arch. Virol., 1989, 108, 59-68, and the Swiss isolates (FIVZ1 and FIVZ2), Morikawa et al., Virus Research, 1991, 21, 53-63.

The nucleotide sequences of three proviral clones derived from American FIV isolates (Petaluma strain) have been described (clones FIV34TF10, FIV14 and isolate PPR) (Olmsted, et al. 1989; Philipps et al., 1990; Talbott et al., 1989) and compared with two Swiss isolates (Morikawa et al. 1991). This comparison led Morikawa et al. to specify the presence of certain conserved regions and certain variable regions within the env gene of FIV. French strains have also been isolated (strains Wo and Me) (Moraillon et al., 1992, Vet. Mic., 31, 41-45).

The virus replicates optimally in blood mononuclear cells and has a tropism for T-lymphocytes, peritoneal macrophage, brain macrophage and astrocytes. In common with other retroviruses, the genetic material of FIV is composed of RNA and the production of a DNA copy of the viral RNA is an essential step in the replication of FIV in the host. This step requires the enzyme reverse transcriptase that is carried into the host by the invading virus. The DNA version of the viral genome is inserted into the genetic material of infected host cells in which it continues to reside as a provirus. This provirus is replicated every time the cell divides and can code for the production of new virus particles. Cells infected with FIV remain infected for the duration of their lifespan.

The virus appears to be spread naturally by horizontal transmission, predominantly by bite wounds from an infected cat as these animals shed appreciable amounts of virus in saliva (Yamamoto et al., Am. J. Vet. Res. 1988, 8:1246). Vertical transmission has been reported, but is rare.

Current diagnostic screening tests for FIV infection detect serum antibody (Ab) to FIV. Virus detection kits are also available but not as prevalent. A number of diagnostic tests are available to determine the presence of FIV antibody in infected animals. For example, PetChek® FIV Ab test kit and the SNAP® Combo FeLV Ag/FIV Ab test kit (IDEXX Laboratories, Westbrook, Me.) are immunoassay based diagnostic tests for FIV infection.

Detecting FIV infection is becoming increasingly important as studies reveal FIV infection is widespread worldwide. According increasingly sensitive and convenient detection techniques are required to address.

SUMMARY OF THE INVENTION

In one aspect, the invention is directed to FIV gag polypeptides. In another aspect, the invention is directed to a method for determining whether an animal is infected with FIV by detecting the presence of FIV antibodies in a biological sample from the animal. In various other aspects, the invention is also directed to a devices and kits for detecting FIV antibodies in a sample. The devices and kits include an FIV gag polypeptide immobilized on a solid phase. The kit includes a specific binding partner for an FIV antibody conjugated to a label.

DETAILED DESCRIPTION

Before describing the present invention in detail, a number of terms will be defined. As used herein, the singular forms "a," "an", and "the" include plural referents unless the context clearly dictates otherwise.

As used herein, the term "polypeptide" refers to a compound of a single chain or a complex of two or more chains of amino acid residues linked by peptide bonds. The chain(s) may be of any length. A protein is a polypeptide, and the terms are used synonymously. Also included within the scope of the invention are functionally equivalent variants and fragments of FIV polypeptides. The polypeptide is capable of binding one or more antibodies specific for the polypeptide.

Polypeptides derived from FIV include any region of the of the FIV proteome including for example, portions of the gag and env regions and mimitopes thereof. U.S. Pat. Nos. 5,648,209, 5,591,572, and 6,458,528, which are incorporated by reference herein in their entirety, describe FIV polypeptides derived from the FIV env and gag proteins. These peptides, and others like them, from gag protein, are suitable for use in the methods of the present invention.

SEQ ID NO:1 through SEQ ID NO:4 are derived from the native FIV gag p24.

```
SEQ ID NO: 1
KMVSIFMEKAREGLGGEEVQLWFTAFSANLTPTDMA

SEQ ID NO: 2
EILDESLKQMTAEYDRTHPPDGPRPLPYFTAAEIMG

SEQ ID NO: 3
KAKSPRAVQLRQGAKEDYSSFIDRLFAQIDQEQNTAEVK

SEQ ID NO: 4
EYDRTHPPDGPRPLPYFTAAEIMGIGLTQEQQAEARFAPAR
```

SEQ ID NO:5 through SEQ ID NO: 9 are derived from the native FIV gag p15.

```
SEQ ID NO: 5
MGNGQGRDWKMAIKRCSNVAVGVGGKSKKFGEGNFR

SEQ ID NO: 6
EGNFRWAIRMANVSTGREPGDIPETLDQLRLVICDLQER

SEQ ID NO: 7
ETLDQLRLVICDLQERREKFGSSKEIDMAIVTLKVFAVAGLLNMT

SEQ ID NO: 8
LLNMTVSTAAAAENMYSQMGLDTRPSMKEAGGKEE

SEQ ID NO: 9
KEEGPPQAYPIQTVNGVPQYVALDP
```

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')2 fragment) specific for the polypeptide.

A "specific binding pair" is a set of two different molecules, where one molecule has an area on its surface or in a cavity that specifically binds to, and is therefore complementary to, an area on the other molecule. "Specific binding partner" refers to one of these two complementarily binding molecules. "Specific binding pair" may refer to a ligand and a receptor, for example. In another example, the specific binding pair might refer to an immunological pair, for example an antigen and antibody.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g., an immunohistochemical assay, an enzyme-linked immunosorbent assay (ELISA), a radioimmunoassay (RIA), or a western blot assay.

Animals infected with FIV are felids, which is to be understood to include all members of the order Felidae, including domestic cats, lions, tigers, jaguars, leopards, puma, ocelots, etc. As used herein, the terms "felid," "cat" or "animal" is a reference to all felids.

A "biological sample" refers to a sample from an animal subject including saliva, whole blood, serum, plasma or other sample known to contain FIV antibodies A "label" is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured.

The label employed in the current invention could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes. The label can directly produce a signal, and therefore additional components are not required to produce a signal. Alternatively, a label may need additional components, such as substrates or co-enzymes, in order to produce a signal. The suitability and use of such labels useful for producing a signal are discussed in U.S. Pat. No. 6,489,309, and U.S. Pat. No. 5,185,243, which are incorporated by reference herein in their entirety. For example, a label may be conjugated to the specific binding partner in a non-covalent fashion. Alternatively, the label may be conjugated to the specific binding partner covalently. U.S. Pat. No 3,817,837, and U.S. Pat. No. 3,996,345, which are incorporated by reference herein in their entirety, describe in detail example of various ways that a label may be non-covalently or covalently conjugated to the specific binding partner.

Solid phase means a porous or non-porous water insoluble material, such as a support or surface. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). The surface can have any one of a number of shapes, such as strip, rod, particle, including bead, and the like. In one aspect, the polypeptides of the invention include a N-terminal cysteine residue to assist in binding the polypeptides to the solid phase.

The method of the invention can be optimized in many ways and one of skill in the art could simultaneously adjust the sample dilutions, reagent concentrations, incubation temperatures and times used in the method to accomplish detection antibodies to FIV in a biological sample.

In one aspect of the invention, an FIV p15 or p24 polypeptide of SEQ ID. NOS: 1-9 is immobilized on a suitable solid support. The biological sample is brought into contact with the polypeptide, to which the anti-FIV antibodies bind, if such antibodies are present in the sample. The binding may be detected by using a second molecule that specifically binds the sample antibodies. The second molecule may be labeled as described herein, or may be include another moiety capable of binding to a label. In a suitable embodiment, a detection reagent includes an FIV protein that is the same or similar to that which is used to capture anti-FIV antibodies (if present). In a specific embodiment of the invention, the detection reagent is an anti-cat IgG antibody. The antibody is conjugated to a label. Following the removal of unbound sample antibody and detection reagent from the solid phase, the presence of the label can be detected.

"Functional equivalent" or "Functionally equivalent" refers to polypeptides related to or derived from the FIV gag polypeptide sequences where the amino acid sequence has been modified by a single or multiple amino acid substitution, insertion, deletion, and also sequences where the amino acids have been chemically modified, such as amino acid analogs, but which nonetheless retain substantially equivalent function. Functionally-equivalent variants may occur as natural biological variations or may be prepared using known techniques such as chemical synthesis, site-directed mutagenesis, random mutagenesis, or enzymatic cleavage and/or ligation of amino acids. Thus, modification of the amino-acid sequence to obtain variant sequences may occur so long as the function of the polypeptide is not affected.

FIV functionally-equivalent variants within the scope of the invention may comprise conservatively substituted sequences, meaning that one or more amino acid residues of the FIV polypeptide are replaced by different residues that do not alter the secondary and/or tertiary structure of the FIV polypeptide. Such substitutions may include the replacement of an amino acid by a residue having similar physicochemical properties, such as charge density, size, configuration, or hypdrophilicity/hydrophobicity. For purposes of example only, such substitutions could include substituting one aliphatic residue (Ile, Val, Leu, or Ala) for another, or substitution of basic residues Lys and Arg, acidic residues Glu and Asp, amide residues Gln and Asn, hydroxyl residues Ser and Tyr, or aromatic residues Phe and Tyr. Conservative variants can generally be identified by modifying a polypeptide sequence of the invention and evaluating the antigenic activity of the modified polypeptide using, for example, an immunohistochemical assay, an enzyme-linked immunosorbent assay (ELISA), a radioimmunoassay (RIA), or a western blot assay. Further information regarding the making of phenotypically silent amino acid exchanges may be found in Bowie et al., *Science* 247:1306-1310 (1990).

Additional variants are also contemplated within the scope of the invention, and such variants include amino and/or carboxyl terminal fusions, for example achieved by addition of amino acid sequences of any number of residues, as well as intrasequence insertion of one or more amino acids. For example, amino acid sequences added may be those derived from the whole or parts of other polypeptides or proteins, or may be those provided in the corresponding positions in the FIV envelope or viral protein. Longer peptides may comprise multiple copies of one or more of the polypeptide sequences. Moreover, multiple copies of the polypeptides may be coupled to a polyamino acid backbone, such as a polylysine backbone to form multiple antigen peptides (MAPs).

Deletional amino acid sequence variants are those in which one or more amino acid residues are removed from the sequence. Insertional variants exist when one or more amino acids are integrated into a predetermined site in the protein, although random insertion is an option with suitable screening of the resulting product. In all cases, these and other FIV variants used retain substantially the same antigenicity of the FIV polypeptides. Other variants are also contemplated, including those where the amino acid substitutions are made in the area outside the antibody recognition regions of the protein. Fusion proteins comprising two or more polypeptide sequences of FIV are also within the scope of the invention provided the sequences provide the appropriate antigenicity. Such polypeptides will generally correspond to at least one epitope or mimitope that is characteristic of FIV. By characteristic, it is meant that the epitope or mimitope will allow immunologic detection of antibody directed to FIV in a physiological sample with reasonable assurance. Usually, it will be desirable that the epitope or mimitope, variant or fusion protein be immunologically distinct from (i.e., not cross-reactive with antibodies which recognize) viruses other than FIV.

An antigenically active variant differs by about, for example, 1, 2, 3, 5, 6, 10, 15 or 20 amino acid residues from SEQ ID NOS: 1 through 9, or a fragment thereof. Where this comparison requires alignment the sequences are aligned for maximum homology. Deletions, insertions, substitutions, repeats, inversions or mismatches are considered differences. The differences are, preferably, differences or changes at a non-essential residue or a conservative substitution. The site of variation can occur anywhere in the polypeptide, as long as the resulting variant polypeptide is antigenically substantially similar to SEQ ID NOS: 1 through 9. Exemplary functionally-equivalent variants include those displaying 50% or more amino acid homology. Preferably, such homology is 60%, 70%, or greater than 80%. However, such variants may display a smaller percentage of homology overall and still fall within the scope of the invention where they have conserved regions of homology.

In some cases, one or more cysteine residues may be added to the termini of the polypeptides in order to facilitate specific carrier linkage or to permit disulphide bonding to mimic antigenic loops and thus increase the antigenicity. Moreover, a fatty acid or hydrophobic tail may be added to the peptides to facilitate incorporation into delivery vehicles and to increase antigenicity.

The FIV polypeptides used as detection reagents may be natural, i.e., including the entire FIV protein or fragments thereof isolated from a natural source, or may be synthetic. The natural proteins may be isolated from the whole FIV virus by conventional techniques, such as affinity chromatography. Polyclonal or monoclonal antibodies may be used to prepare a suitable affinity column by well-known techniques.

Proteins that are immunologically cross-reactive with a natural FIV protein can be chemically synthesized. For example, polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain. Merrifield, 1963, J. Am. Chem. Soc., 85:2149-2156). Recombinant proteins can also be used. These proteins may be produced by expression in cultured cells of recombinant DNA molecules encoding a desired portion of the FIV genome. The portion of the FIV genome may itself be natural or synthetic, with natural genes obtainable from the isolated virus by conventional techniques. Of course, the genome of FIV is RNA, and it will be necessary to transcribe the natural RNA into DNA by conventional techniques employing reverse transcriptase. Polynucleotides may also be synthesized by well-known techniques. For example, short single-stranded DNA fragments may be prepared by the phosphoramidite method described by Beaucage and Carruthers, 1981, Tett. Letters 22:1859-1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired FIV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the FIV DNA fragment encoding the desired polypeptide product, transcriptional and translational initiation regulatory sequences joined to the 5'-end of the FIV DNA termination regulatory sequences joined to the 3'-end of the fragment. The transcriptional regulatory sequences will include a heterologous promoter that is recognized by the host. Conveniently, a variety of suitable expression vectors are commercially available for a number of hosts.

To be useful in the detection methods of the present invention, the polypeptides are obtained in a substantially pure form, that is, typically from about 50% w/w or more purity, substantially free of interfering proteins and contaminants. Preferably, the FIV polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. In one embodiment, an FIV protein is immobilized on a solid support at a distinct location. Detection of protein-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories), useful in the present invention. Colloidal particle based tests can also be used, such as the commercially available WITNESS® FIV diagnostic test (Synbiotics Corporation, Lyon, France).

Immobilization of one or more analyte capture reagents, e.g., FIV proteins, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

In another aspect, the invention includes one or more labeled specific binding reagents that can be mixed with a test sample prior to application to a device for of the invention. In this case it is not necessary to have labeled specific binding reagents deposited and dried on a specific binding reagent pad in the device. A labeled specific binding reagent, whether added to a test sample or pre-deposited on the device, can be for example, a labeled FIV protein that specifically binds an antibody for FIV.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

The following are provided for exemplification purposes only and are not intended to limit the scope of the invention described in broad terms above. All references cited in this disclosure are incorporated herein by reference.

EXAMPLE

Blood samples were obtained from FIV negative cats and cats naturally infected with FIV. The samples were confirmed FIV antibody negative or positive by a western immunoblot confirmatory test. When necessary, serum and plasma samples were stored frozen until testing.

Microplate ELISA analysis was performed on serum samples collected from confirmed FIV negative and infected cats in an indirect assay format with individual FIV polypeptides SEQ ID NOS: 1-9 on the solid phase and a commercial anti-(feline IgG) peroxidase conjugate reagent (Jackson Immunoresearch, Bangor, Me., USA).

The polypeptides were synthesized using a commercial instrument and following the manufacturer's instructions. Polypeptide stocks were prepared at 5 mg/ml in DMSO. The polypeptides were then coated on microplate wells (peptide @ 10 ug/ml in 50 mM Tris-HCl pH 7.4, 100 ul/well). The plates were then blocked/overcoated with 2% Tween-20/2.5% sucrose, allowed to dry in mylar bags with desiccant. BSA-conjugated peptide could also be used.

For the assays, feline serum samples (100 ul/well, diluted 1/1000 in 50% fetal bovine serum were added to the wells and the plates were incubated for fifteen minutes at room temperature. Following incubation, the microplates were washed with PBS/Tween. Goat Anti-(cat IgG):peroxidase conjugate was added to the wells (diluted 1/4000 anti-catIgG:peroxidase in 50% fetal bovine serum. The plates were incubated for another fifteen minutes at room temperature and washed a second time with PBS/Tween. Peroxidase substrate was added (100 ul/well, tetramethyl benzidine peroxidase substrate) and the plates were incubated a third time for ten minutes at room temperature. A hydrofluoric acid stop solution (50 ul/well) was added to the plates. Sample antibody binding was measured by determining peroxidase activity (colored product) with a spectrophotometer (A650 nm). The positive/negative cut-off was determined to be the mean absorbance of the negative samples plus three standard deviations for those samples. The IDEXX PetChek® Anti-FIV antibody test kit was also run on these samples as a reference test.

Tables 1 through 9 show microplate ELISA results for SEQ. ID: 1 through SEQ. ID: 9 polypeptides, respectively. Each of these polypeptides could be used to detect FIV antibody in FIV-infected felines.

TABLE 1

| sample | SEQ ID 1 A(650 nm) | SEQ ID 1 result | PetChek A(650 nm) | PetChek result | | |
|---|---|---|---|---|---|---|
| 2426:100 | 1.085 | positive | 0.546 | positive | | |
| 14828 | 0.329 | positive | 1.295 | positive | | |
| Jack | 2.342 | positive | 1.539 | positive | | |
| 18110-97 | 0.501 | positive | 1.067 | positive | | |
| Detroit | 0.704 | positive | 2.068 | positive | | |
| B30190-8 | 0.371 | positive | 1.561 | positive | | |
| 1219 ARL | 0.235 | positive | 1.715 | positive | | |
| 3794-145B | 0.556 | positive | 1.084 | positive | | |
| Cornell NEG | 0.059 | negative | 0.048 | negative | mean NEGs | 0.071 |
| Avery 2253-9 NEG | 0.058 | negative | 0.045 | negative | SD | 0.052 |
| 3794:145A NEG | 0.199 | negative | 0.051 | negative | 3SD | 0.156 |
| Weege NEG | 0.063 | negative | 0.045 | negative | mean + 3SD | 0.227 |

TABLE 2

| sample | SEQ ID 2 A(650 nm) | SEQ ID 2 result | PetChek A(650 nm) | PetChek result | | |
|---|---|---|---|---|---|---|
| 18110-97 | 0.721 | positive | 1.067 | positive | | |
| 2899-129 stray | 0.528 | positive | 1.368 | positive | | |
| B30190-8 | 0.383 | positive | 1.561 | positive | | |
| 1219 ARL | 0.247 | positive | 1.715 | positive | | |
| Cornell NEG | 0.053 | negative | 0.048 | negative | mean NEGs | 0.085 |
| Avery 2253-9 NEG | 0.196 | negative | 0.045 | negative | SD | 0.062 |
| 3794:145A NEG | 0.065 | negative | 0.051 | negative | 3SD | 0.187 |
| Weege NEG | 0.065 | negative | 0.045 | negative | mean + 3SD | 0.272 |

TABLE 3

| sample | SEQ ID 3 A(650 nm) | SEQ ID 3 result | PetChek A(650 nm) | PetChek result | | |
|---|---|---|---|---|---|---|
| 18110-97 | 0.340 | positive | 1.067 | positive | | |
| B30190-8 | 0.515 | positive | 1.561 | positive | | |
| 3794-145B | 0.413 | positive | 1.084 | positive | | |
| 2426:100 | 0.285 | positive | 0.546 | positive | | |
| 14828 | 0.269 | positive | 1.295 | positive | | |
| 3794-151L | 0.293 | positive | 1.056 | positive | | |
| Cornell NEG | 0.056 | negative | 0.048 | negative | mean NEGs | 0.060 |
| Avery 2253-9 NEG | 0.070 | negative | 0.045 | negative | SD | 0.014 |

TABLE 3-continued

| sample | SEQ ID 3 A(650 nm) | SEQ ID 3 result | PetChek A(650 nm) | PetChek result | | |
|---|---|---|---|---|---|---|
| 3794:145A NEG | 0.085 | negative | 0.051 | negative | 3SD | 0.043 |
| Weege NEG | 0.066 | negative | 0.045 | negative | mean + 3SD | 0.103 |

TABLE 4

| sample | SEQ ID 4 A(650 nm) | SEQ ID 4 result | PetChek A(650 nm) | PetChek result | | |
|---|---|---|---|---|---|---|
| 1219 ARL | 0.482 | positive | 1.715 | positive | | |
| 1033 ARL | 0.446 | positive | 2.029 | positive | | |
| 18110-91 | 0.555 | positive | 1.583 | positive | | |
| 14828 | 0.765 | positive | 1.295 | positive | | |
| Jack | 0.661 | positive | 1.539 | positive | | |
| 17992-89 | 0.512 | positive | 1.843 | positive | | |
| 18110-97 | 0.593 | positive | 1.067 | positive | | |
| Detroit | 0.647 | positive | 2.068 | positive | | |
| Rodney | 0.499 | positive | 1.819 | positive | | |
| 2899-129 stray | 1.713 | positive | 1.368 | positive | | |
| B30190-8 | 0.567 | positive | 1.561 | positive | | |
| 3794-145B | 1.292 | positive | 1.084 | positive | | |
| 3794-151L | 1.163 | positive | 1.056 | positive | | |
| 3794-151F | 0.756 | positive | 1.930 | positive | | |
| Cornell NEG | 0.078 | negative | 0.048 | negative | mean NEGs | 0.097 |
| Avery 2253-9 NEG | 0.158 | negative | 0.045 | negative | SD | 0.079 |
| 3794:145A NEG | 0.084 | negative | 0.051 | negative | 3SD | 0.236 |
| Weege NEG | 0.268 | negative | 0.045 | negative | mean + 3SD | 0.333 |

TABLE 5

| sample | SEQ ID 5 A(650 nm) | SEQ ID 5 result | PetChek A(650 nm) | PetChek result | | |
|---|---|---|---|---|---|---|
| 2426:100 | 2.560 | positive | 0.546 | positive | | |
| 1219 ARL | 0.400 | positive | 1.715 | positive | | |
| 1033 ARL | 0.211 | positive | 2.029 | positive | | |
| 14828 | 0.198 | positive | 1.295 | positive | | |
| Jack | 0.225 | positive | 1.539 | positive | | |
| 18110-97 | 0.828 | positive | 1.067 | positive | | |
| 2899-129 stray | 0.320 | positive | 1.368 | positive | | |
| PET 2172-72 | 0.725 | positive | 1.156 | positive | | |
| 3794-145B | 0.344 | positive | 1.084 | positive | | |
| 3794-151F | 0.189 | positive | 1.930 | positive | | |
| Cornell NEG | 0.048 | negative | 0.048 | negative | mean NEGs | 0.054 |
| SPF Avery 2253-9 | 0.070 | negative | 0.045 | negative | SD | 0.010 |
| 3794:145A | 0.053 | negative | 0.051 | negative | 3SD | 0.031 |
| Weege | 0.069 | negative | 0.045 | negative | mean + 3SD | 0.084 |

TABLE 6

| sample | SEQ ID 6 A(650 nm) | SEQ ID 6 result | PetChek A(650 nm) | PetChek result | | |
|---|---|---|---|---|---|---|
| 2426:100 | 0.808 | positive | 0.546 | positive | | |
| 2426-91A | 0.151 | positive | 2.001 | positive | | |
| 1219 ARL | 0.256 | positive | 1.715 | positive | | |
| Jack | 0.502 | positive | 1.539 | positive | | |
| 17992-89 | 0.275 | positive | 1.843 | positive | | |
| 18110-97 | 0.521 | positive | 1.067 | positive | | |
| Detroit | 0.703 | positive | 2.068 | positive | | |
| Rodney | 0.256 | positive | 1.819 | positive | | |
| 2899-129 stray | 0.157 | positive | 1.368 | positive | | |
| PET 2172-72 | 0.739 | positive | 1.156 | positive | | |
| 3794-145B | 0.213 | positive | 1.084 | positive | | |
| 3794-151L | 0.175 | positive | 1.056 | positive | | |
| 3794-151F | 0.306 | positive | 1.930 | positive | | |
| Cornell NEG | 0.065 | negative | 0.048 | negative | mean NEGs | 0.056 |
| SPF Avery 2253-9 | 0.080 | negative | 0.045 | negative | SD | 0.012 |

TABLE 6-continued

| sample | SEQ ID 6 A(650 nm) | SEQ ID 6 result | PetChek A(650 nm) | PetChek result | | |
|---|---|---|---|---|---|---|
| 3794:145A | 0.050 | negative | 0.051 | negative | 3SD | 0.037 |
| Weege | 0.064 | negative | 0.045 | negative | mean + 3SD | 0.093 |

TABLE 7

| sample | SEQ ID 7 A(650 nm) | SEQ ID 7 result | PetChek A(650 nm) | PetChek result | | |
|---|---|---|---|---|---|---|
| 2426:100 | 2.703 | positive | 0.546 | positive | | |
| 2426-91A | 0.459 | positive | 2.001 | positive | | |
| 2426-91C | 0.487 | positive | 1.067 | positive | | |
| 1219 ARL | 0.714 | positive | 1.715 | positive | | |
| 1033 ARL | 0.553 | positive | 2.029 | positive | | |
| 14828 | 0.315 | positive | 1.295 | positive | | |
| Jack | 0.859 | positive | 1.539 | positive | | |
| 18110-97 | 1.251 | positive | 1.067 | positive | | |
| 2899-129 stray | 0.407 | positive | 1.368 | positive | | |
| PET 2172-72 | 0.444 | positive | 1.156 | positive | | |
| B30190-8 | 0.734 | positive | 1.561 | positive | | |
| 3794-145B | 0.502 | positive | 1.084 | positive | | |
| 3794-151L | 0.368 | positive | 1.056 | positive | | |
| 3794-151F | 0.648 | positive | 1.930 | positive | | |
| Cornell NEG | 0.146 | negative | 0.048 | negative | mean NEGs | 0.102 |
| SPF Avery 2253-9 | 0.132 | negative | 0.045 | negative | SD | 0.060 |
| 3794:145A | 0.184 | negative | 0.051 | negative | 3SD | 0.181 |
| Weege | 0.165 | negative | 0.045 | negative | mean + 3SD | 0.283 |

TABLE 8

| sample | SEQ ID 8 A(650 nm) | SEQ ID 8 result | PetChek A(650 nm) | PetChek result | | |
|---|---|---|---|---|---|---|
| 1219 ARL | 0.294 | positive | 1.715 | positive | | |
| 18110-91 | 0.461 | positive | 1.583 | positive | | |
| 14828 | 0.310 | positive | 1.295 | positive | | |
| Jack | 0.467 | positive | 1.539 | positive | | |
| 18110-97 | 0.403 | positive | 1.067 | positive | | |
| 3794-145B | 0.491 | positive | 1.084 | positive | | |
| 3794-151L | 0.992 | positive | 1.056 | positive | | |
| 3794-151F | 0.301 | positive | 1.930 | positive | | |
| Cornell NEG | 0.076 | negative | 0.048 | negative | mean NEGs | 0.066 |
| SPF Avery 2253-9 | 0.066 | negative | 0.045 | negative | SD | 0.024 |
| 3794:145A | 0.116 | negative | 0.051 | negative | 3SD | 0.073 |
| Weege | 0.078 | negative | 0.045 | negative | mean + 3SD | 0.139 |

TABLE 9

| sample | SEQ ID 9 A(650 nm) | SEQ ID 9 result | PetChek A(650 nm) | PetChek result | | |
|---|---|---|---|---|---|---|
| 2426:100 | 0.417 | positive | 0.546 | positive | | |
| 2426-91A | 1.040 | positive | 2.001 | positive | | |
| 2426-91C | 0.481 | positive | 1.067 | positive | | |
| 1219 ARL | 0.269 | positive | 1.715 | positive | | |
| 14828 | 0.224 | positive | 1.295 | positive | | |
| Jack | 0.234 | positive | 1.539 | positive | | |
| 17992-89 | 0.318 | positive | 1.843 | positive | | |
| 18110-97 | 0.653 | positive | 1.067 | positive | | |
| Detroit | 0.504 | positive | 2.068 | positive | | |
| Rodney | 0.323 | positive | 1.819 | positive | | |
| 2899-129 stray | 0.506 | positive | 1.368 | positive | | |
| 3794-145B | 0.393 | positive | 1.084 | positive | | |
| 3794-151F | 0.211 | positive | 1.930 | positive | | |
| Cornell NEG | 0.053 | negative | 0.048 | negative | mean NEGs | 0.060 |
| SPF Avery 2253-9 | 0.081 | negative | 0.045 | negative | SD | 0.017 |
| 3794:145A | 0.086 | negative | 0.051 | negative | 3SD | 0.051 |
| Weege | 0.073 | negative | 0.045 | negative | mean + 3SD | 0.111 |

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A synthetic polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

2. A method of detecting the presence of FIV antibodies in a biological sample, the method comprising:
   contacting a biological sample from an animal with the FIV polypeptide of claim 1, and
   detecting whether FIV antibodies in the sample substantially bind to the polypeptide, thereby detecting the presence of FIV antibodies in the sample.

3. A method for detecting an FIV infection in an animal comprising:
   (a) contacting a biological sample from the animal with a solid phase having bound thereto the FIV polypeptide of claim 1;
   (b) contacting the sample and the solid phase with a specific binding partner for an FIV antibody, wherein the specific binding partner is conjugated to a label;
   (c) detecting the label, thereby detecting an FIV infection in the animal.

4. The method of claim 3 wherein the specific binding partner for an FIV antibody is an anti-cat IgG antibody.

5. A method for detecting an FIV infection in an animal comprising:
   (a) contacting a biological sample from the animal with a specific binding partner for an FIV antibody, wherein the specific binding partner is conjugated to a label;
   (b) contacting the sample and the specific binding partner for the sample antibody conjugated to a label with the solid phase having bound thereto the FIV polypeptide of claim 1; and
   (c) detecting the label, thereby detecting a FIV infection in the animal.

6. The method of claim 5 wherein the specific binding partner for an FIV antibody is an anti-cat IgG antibody.

7. The synthetic polypeptide of claim 1, wherein the polypeptide has the sequence of SEQ ID NO:1.

8. The synthetic polypeptide of claim 1, wherein the polypeptide has the sequence of SEQ ID NO:2.

9. The synthetic polypeptide of claim 1, wherein the polypeptide has the sequence of SEQ ID NO:3.

10. The synthetic polypeptide of claim 1, wherein the polypeptide has the sequence of SEQ ID NO:4.

11. The synthetic polypeptide of claim 1, wherein the polypeptide has the sequence of SEQ ID NO:5.

12. The synthetic polypeptide of claim 1, wherein the polypeptide has the sequence of SEQ ID NO:6.

13. The synthetic polypeptide of claim 1, wherein the polypeptide has the sequence of SEQ ID NO:7.

14. The synthetic polypeptide of claim 1, wherein the polypeptide has the sequence of SEQ ID NO:8.

15. The synthetic polypeptide of claim 1, wherein the polypeptide has the sequence of SEQ ID NO:9.

* * * * *